United States Patent

Somborac et al.

[11] Patent Number: 5,961,328
[45] Date of Patent: *Oct. 5, 1999

[54] DENTAL IMPLANT

[76] Inventors: Milan Somborac; Stefan Somborac, both of 229-6th St., Collingwood, Ontario, Canada, L9Y 1Z2

[ * ] Notice: This patent is subject to a terminal disclaimer.

[21] Appl. No.: 08/871,848

[22] Filed: Jun. 9, 1997

Related U.S. Application Data

[63] Continuation-in-part of application No. 08/404,669, Jan. 23, 1995, Pat. No. 5,636,989.

[51] Int. Cl.[6] .................................................... A61C 8/00

[52] U.S. Cl. ................................................ 433/173

[58] Field of Search .................................. 433/172, 173, 433/174, 175, 176

[56] References Cited

U.S. PATENT DOCUMENTS

| | | | |
|---|---|---|---|
| Re. 33,796 | 1/1992 | Niznick | 433/173 |
| 4,079,515 | 3/1978 | Friedman . | |
| 4,468,200 | 8/1984 | Münch | 433/174 |
| 4,624,673 | 11/1986 | Meyer | 433/173 |
| 4,687,443 | 8/1987 | Driskell | 433/173 |
| 5,030,096 | 7/1991 | Hurson et al. | 433/173 |
| 5,049,073 | 9/1991 | Lauks | 433/173 |
| 5,197,881 | 3/1993 | Chalifoux | 433/173 |
| 5,205,745 | 4/1993 | Kamiya et al. | 433/173 |
| 5,209,659 | 5/1993 | Friedman et al. | 433/173 |
| 5,246,369 | 9/1993 | Poulmaire | 433/173 |
| 5,302,126 | 4/1994 | Wimmer et al. | 433/173 |
| 5,316,476 | 5/1994 | Krauser | 433/173 |
| 5,344,457 | 9/1994 | Pilliar et al. | 433/174 |
| 5,427,527 | 6/1995 | Niznick et al. | 433/174 |
| 5,437,551 | 8/1995 | Chalifoux | 433/172 |
| 5,564,928 | 10/1996 | Gittleman | 433/180 |
| 5,636,989 | 6/1997 | Somborac et al. | 433/173 |

OTHER PUBLICATIONS

Article entitled Magnet retained Overdentures using the Astra Dental Implant System written by A.D. Walmsley et al., and contained in British Dental Journal, Jun. 5, 1993, pp. 399–404.

Article entitled *The Effects of Surface Configuration on the Retentive Properties of Parallel—Sided Dowels Cemented with a Composite Luting Agent* written by Kan–Shan Shih, School of Dentistry, National Defence Medical Center and Department of Dentistry, Tri–Service General Hospital Taipei, Taiwan, Republic of China, Received accepted, Dec. 17, 1988.

Excerpt from a paper entitled The Effect of Diameter and Length of Hydroxylapatite–Coated Dental Implants on Ultimate Pullout Force in Dog Alveolar Bone written by Michael S. Block et al., and contained in "J. Oral Maxillofac. Surg." (48: pp. 174–178, 1990).

Excerpt from a paper entitled A Multicenter 5–Year Retrospective Survival Analysis of 6,200 Integral Implants written by E. Robert Stultz et al., and contained in "Compend Contin. Educ. Dent" (vol. XIV, No. 4).

*Primary Examiner*—Nicholas D. Lucchesi

[57] ABSTRACT

A dental implant for installation into a mouth is disclosed. The implant includes a one piece implant body to which is attached an abutment portion for anchoring a denture or tooth replacement. The implant body includes a coronal portion having a keyway. The abutment portion includes a key which mates with the keyway to form a non-rotational joint. In one aspect of invention, the abutment portion is cemented into the keyway. In another aspect of the invention, the key is tapped in to the keyway to form a cold weld. There is also shown a method of installing a dental implant which includes press fitting the implant body into a preformed cylindrical bore at the implant site. The abstract is made retrievable without disturbing the bone implant interface.

8 Claims, 14 Drawing Sheets

DENTAL IMPLANT

This is a continuation in part of application Ser. No. 08/404,669 filed Jan. 23, 1995 now U.S. Pat. No. 5,636,989.

FIELD OF THE INVENTION

This invention relates to dental implant of the type used in the mouth to stabilize dentures or support dental crowns and bridges.

BACKGROUND OF THE INVENTION

Dental implants used to stabilize dentures or support dental crowns and bridges have been known and have been used fairly extensively in the recent past. Such prior art devices are typically comprised of three components, namely, an implant component for anchoring to the bone, a transgingival component and a separate support component. The support component usually attaches to the transgingival component which, in turn attaches to the anchoring component at about the level of the bone. An artificial tooth or bridge may then be attached to this separate support component. This support component is sometimes referred to as an abutment portion, the transgingival component is sometimes referred to as an abutment portion, the transgingival component is sometimes referred to as an abutment connection or the transgingival collar or the transepithelial connection and the implant is sometimes referred to as a fixture.

An example of such a prior device may be found in Canadian Patent No. 1,313,597. This patent describes as implant for insertion into bone through an epithelial and fibrous connective tissue layer to which a prosthesis may be attached. This implant comprises a top portion for supporting a mechanical component to which the prosthesis may be connected and a body comprising an upper bone attachment region which tapers to a lower bone engagement region having a porous surface. The upper bone attachment region comprises a substantially non-porous but bioreative surface and this patent teaches that this results in an upper bone attachment region which is claimed to be capable of enhancing bone attachment.

However, several problems develop with an implant of this type. In particular, the patent teaches use of a collar 14 that is adapted to be coupled to the implant 12. However the interface between the collar 14 and the implant 12 occurs at a level below the gingiva in the installed position. Further, although the patent teaches providing recesses 40 on the lower surface 42 of the collar 14 to compliment projections 32 of the implant 12 to prevent rotation between the two components, in practice this is not effective. The attachment between the collar and the implant is accomplished by means of a threaded screw identified as 46 in FIG. 1. Such a screw has a natural tendency to become loose during the vigorous stresses to which an implant of this type is subjected.

To avoid problems associated with the loosening of the threaded screw 46, practitioners have resorted to insertion of cement into the threaded portion to ensure a locked and non-loosening joint between the implant component and the support component. Unfortunately, because the interface between the collar and the implant is below the gum level, any excess cement will be squeezed out at the interface and may not be noticed by the practitioner since it is hidden from view. Such excess accumulation of cement can create irritation of the gum and the bone and can result in infection and/or implant failure.

In addition, all implant system, (fixture, abutment connection, abutment) which have this type of arrangement have a microgap between the fixture or implant and the abutment connection or the transgingival collar at the level of the bone. This microgap has been called an "endotoxin generator" by some authorities because it is a region for potential bacterial growth.

Other prior art devices include implants with threaded exteriors which require extensive and complicated methods for preparation of the gum and bone to accept the insert. As a result, such implants are difficult and expensive to insert and the surgery is most often done by specialists. In any event they are not practical and result in excess discomfort for the patient and unnecessary difficulties for the dentist making the installation. For example, some require incising the gym to gain access to the bone; multiple drilling and reaming steps; installation of the implant; reattachment, by suturing or the like, of the gum over the implant site to promote healing; a return visit several months later to the dental office to have the gum again incised to allow access to the implant; insertion and attachment of the abutment portion; and final attachment of the prosthesis to the abutment portion. The first incision into the gym can promote scaring, making the second incision difficult.

SUMMARY OF THE INVENTION

What is required is an implant which may be installed in an easy one-step method and yet which is secured to the bone and provides a firm anchor. Preferably such an invention would also minimize the risk of infection or irritation of the bone and the gingiva and would provide for easy attachment with standard components. Further, such an implant would not require an excessive number of steps for installation, or excessive patient discomfort and would be quickly and efficiently installed in various types of installation conditions.

Therefore, according to the present invention there is an implant for anchoring a prosthetic device in bone, said implant comprising:
 (a) a one piece body having:
  (i) a root portion having a surface conducive to bone ingrowth, and having a press fitting portion;
  (ii) a press fitting emergent portion having a smooth biocompatible surface which is non-irritating to living tissue, and
  (iii) a coronal portion having a keyway; and
 (b) an abutment portion of insertion into said keyway, said abutment portion including a key at one end of insertion into said keyway and a head for retention of said prosthetic device at the other end.

In a further aspect of the present invention there is provided a method of inserting a dental implant comprising:
 incising through a gingival layer;
 drilling a pilot hold, at an appropriate position into a bone located below said gingival layer;
 drilling a recess, about said pilot hole, into the bone with a second drill bit to form a tapered recess of appropriate diameter;
 positioning a one piece dental implant in the tapered recess;
 gently tapping said implant into surface engagement with said bone wherein said step of tapping includes welding a smooth emergent portion against a hard cortical bone portion and wedging a root portion coated with a material conducive to bone ingrowth into a cancellous region of the bone;
 allowing said bone to grow into said root portion; and
 securing an abutment portion to said implant.

BRIEF DESCRIPTION OF THE DRAWINGS

Reference will now be made to preferred embodiments of the invention by reference to the attached drawings which are by way of example only and in which.

DETAILED DESCRIPTION OF THE PREFERRED EMBODIMENTS

Figure 1:
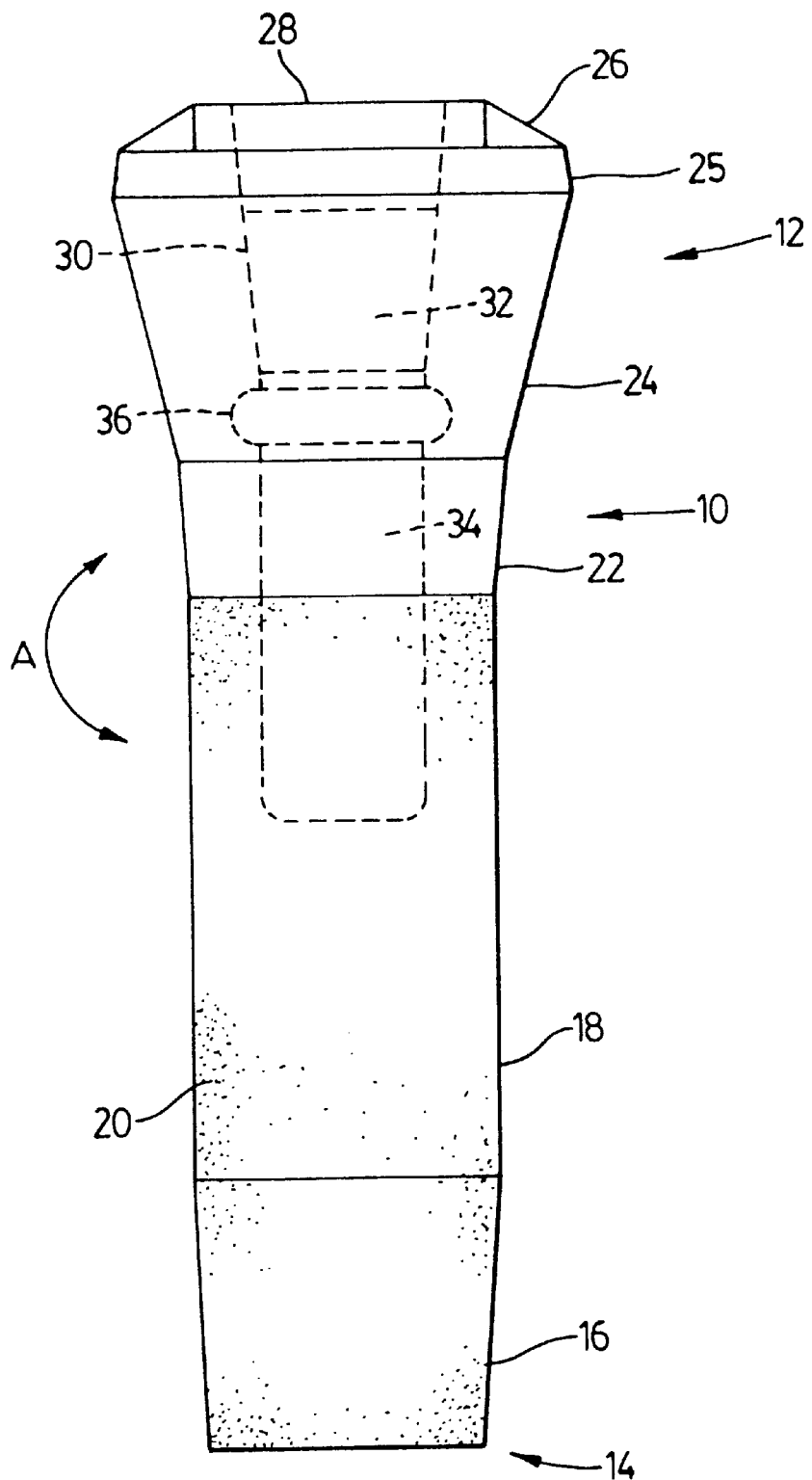
FIG. 1 is a side view showing an implant according to the present invention.

FIG. 1 shows a one piece body or implant 10 having a coronal portion 12 and an apical portion 14. Beginning at the bottom of the one piece body 10 there is shown a tapered section 16 above which is cylindrical section 18. The tapered section 16 and the cylindrical section 18 are suitably coated with a material which is conducive to bone ingrowth and which is identified as 20. These sections 16, 18 together may be considered as a root portion. The preferred form of bony ingrowth material is of the type which creates a multitude of tiny passageways. This can be accomplished, for example, by fine wire mesh screens or the like, but the preferred form is to use discrete particles of titanium alloy which are bonded to the outside of the implant in a random fashion. The preferred method of bonding is by sintering, as will be known by those skilled in the art. The preferred size of particles is between 45 to 150 microns although other sizes may also be appropriate for bony in growth, as will be known to those skilled in the art.

The one piece implant consisting of the coronal portion 12, the body 10, with the apical portion 14, is preferably made of titanium alloy, Ti6Al4Va, and the coating material is made of commercially pure titanium.

Above the cylindrical section 18 coated with bony ingrowth material 20 is a tapered, smooth-walled portion 22. The taper of portion 22 may be referred to as the "fourth taper". The smooth wall is an important aspect of the present invention. To avoid gum and bone infection it is important to have a relatively smooth nonporous surface which is biocompatible at the emergent portion. In particular, it is preferred if the emergent region is machine polished rather than highly polished. Also it is preferred if the emergent cylindrical portion 18 and the tapered portion have an angle therebetween (shown as A in FIG. 1) which is preferably more than 168 degrees and which is most preferably about 176 degrees. The preferred length of the smooth walled portion is 0.06 in. (1.50 m.m.). It is also preferred if the tapered portion 16 has an identical angle of taper of no more than 12 degrees from vertical, and most preferably about four degrees from vertical where vertical in this sense means the vertical side edge of the cylindrical portion 18.

The coronal portion 12 begins with a tapered section 24 increasing in diameter towards the end of the coronal portion 12, and which ends at a generally horizontal top portion 28. Between tapered section 24 and the top 28 are located two further tapered sections, identified as 25 and 26 respectively. The preferred total length of the coronal portion 12 is 0.16 in. (4.00 m.m.), of which the axial length of tapered section 24 is 0.12 in. (3.00 m.m.) and of each of sections 25, 26 is 0.02 in. (0.50 m.m.).

Located within the coronal portion is a keyway identified as 30 which includes a tapered section 32 and apart cylindrical section 34. The taper on section 32 may also be referred to as the "first taper". Located between these two sections is a toroidal section 36 which may be formed in a part circular shape with cross-section having a 0.01 in. (0.30 m.m.) diameter.

Figure 2:
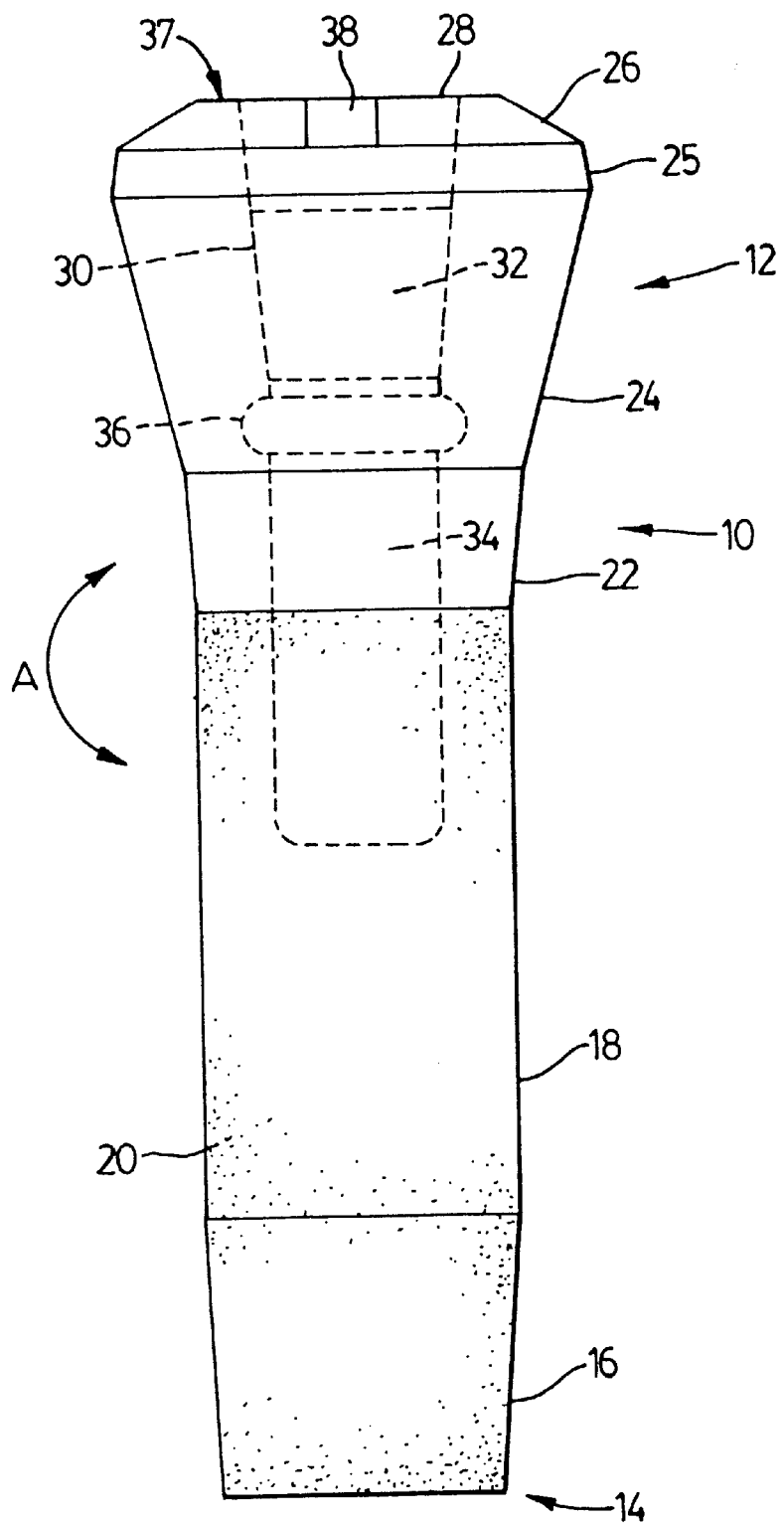
FIG. 2 is a front view of the implant of FIG. 1.

Located at the tope of the coronal portion 12 is a cross groove 38 which is shown more clearly in FIG. 2. The purpose of this groove is to provide an additional keyway to resist rotation of the parts of the present invention with respect to each other as will be appreciated from the following description.

Figure 3:
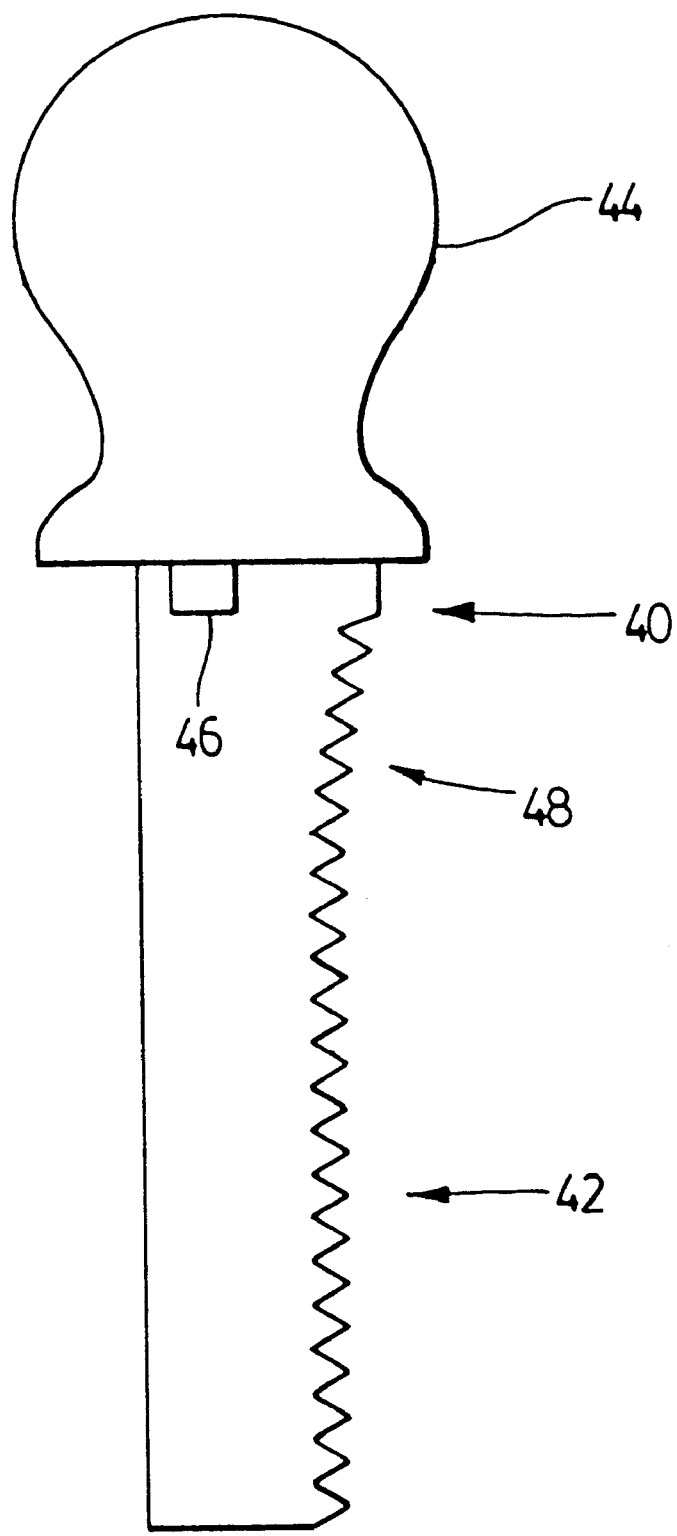
FIG. 3 is a front view of an abutment portion for an implant of FIG. 1 adapted to act as an anchor for overdenture retention.

Turning to FIG. 3, an abutment portion indicated generally as 40 is shown. The abutment portion is formed with a key 42 (also referred to as a keyway insertion portion) for insertion into the keyway 30 of the implant 10 and a head 44 which is in the form of a common anchor for over denture retention. As can be seen in FIG. 3, a locking bar 46 is provide which mates with groove 38 on the coronal portion of implant 10. Also, it can be seen that a tapered section indicated at 48, also referred to as a second taper, is provided on the key for the purpose of locking the abutment portion 40 into the implant 10.

Figure 4:
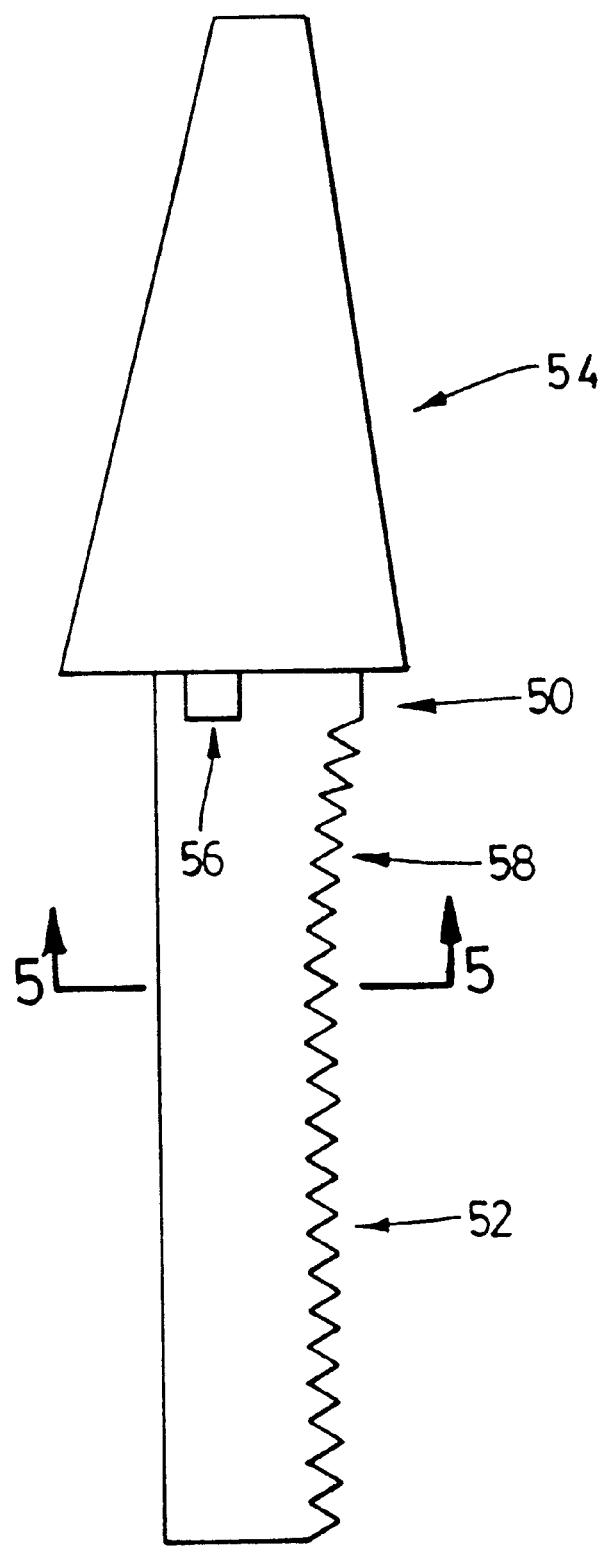
FIG. 4 is a front view of an abutment portion for an implant of FIG. 1 adapted to act as an anchor for a false tooth cap.

FIG. 4 is a view of a second abutment portion 50 of the type used to act as an anchor for a single false tooth cap. The keyportion 52 is identical to the key portion 42 of the abutment 49 and includes a locking bar 56 which is identical to locking bar 46. The head portion 54 is in the form of a standard anchor for a single tooth cap. Again, a tapered portion 58 is provided which is identical to the tapered portion 48.

Figure 5:
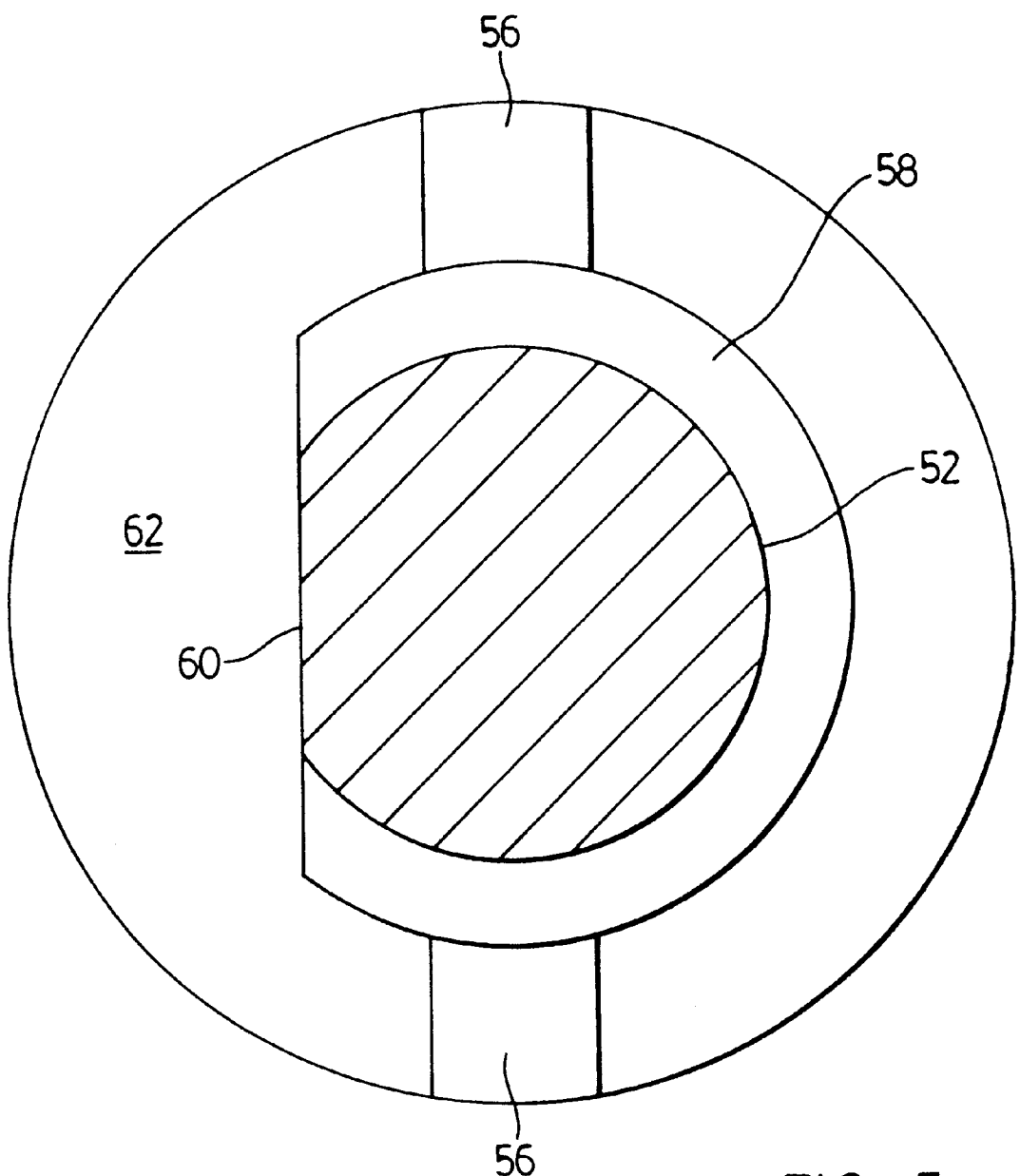
FIG. 5 is a cross-sectional view through the abutment portion along the lines of 4—4 of FIG. 4.

FIG. 5 shows a cross-sectional view along line 4—4 of FIG. 4. As will be appreciated this view is identical for abutment portions 40 and 50, which according to the present invention have the same key portion. As can be seen, one face of the key portion 52, 42 is flat and is indicated as 60. Also shown is the underside of the head 44 which is shown as 62 as well as the locking bar which is shown as 56. The main portion of the key is shown as represented by the line 52 and the taper is represented by the area shown as 58. It can now be appreciated that the taper runs around the perimeter of the key except for at the plane surface 60.

It can now be appreciated how the abutment portions 40, 50 may be securely retained in the implant 10. The first aspect is that there is a non-rotational feature, namely the locking bars 46, 56 and the grooves 38. This feature prevents the rotation of the abutment portion relative to the insert, when the abutment portion is fully inserted into the insert. It is preferred to use this feature to achieve secure non-rotational attachment.

It can now be appreciated that two types of locking are present between the abutment and the implant. The taper of the portion shown as 48 and 58 is preferably less than seven degrees and more than two degrees. Most preferably this degree of taper is about four or five degrees. This degree of taper is desired to take advantage of a metallurgical phenomenon known as cold welding which occurs between relatively smooth metal surfaces which have an interference fit and which are closely angled to each other. It is a feature of the present invention that a cold weld be formed between the mating surfaces of the key and the keyway. The weld can be effected by gently tapping the abutment portion into the implant portion. As will be appreciated, the achieve this weld the surfaces between which the weld is to be formed need to be carefully and properly finished, such as by sandblasting or the like.

The second manner of attaining secure attachment is the use of standard dental cement. It will be understood of course that this is an alternative to the cold welding method outlined about. In this method the cement can be inserted into the implant prior to the abutment portion key 52, 42 being inserted. The cementable abutment portions 40, 50 are about 0.001 in. (0.035 m.m.) smaller in radius than the keyway 30 to allow for cement space. The cement then forms a solid bond between the metal surfaces. It is preferred in this approach to roughen the metal surfaces by serrating or the like to ensure a good bond with the cement. The toroidal section 36 can now be more fully understood. Its purpose is to provide a reservoir into which excess cement may be driven upon insertion of the key into the keyway. Suitable cements for the metal to metal bonding are composite in excess cement present, according to the present invention it will be forced out at an interface between the underside 62 of the head of the abutment portion and the tope of the coronal portion, shown as 37 above the gum line and thus will be clearly visible to the practitioner and readily removed while still soft.

Figure 6:
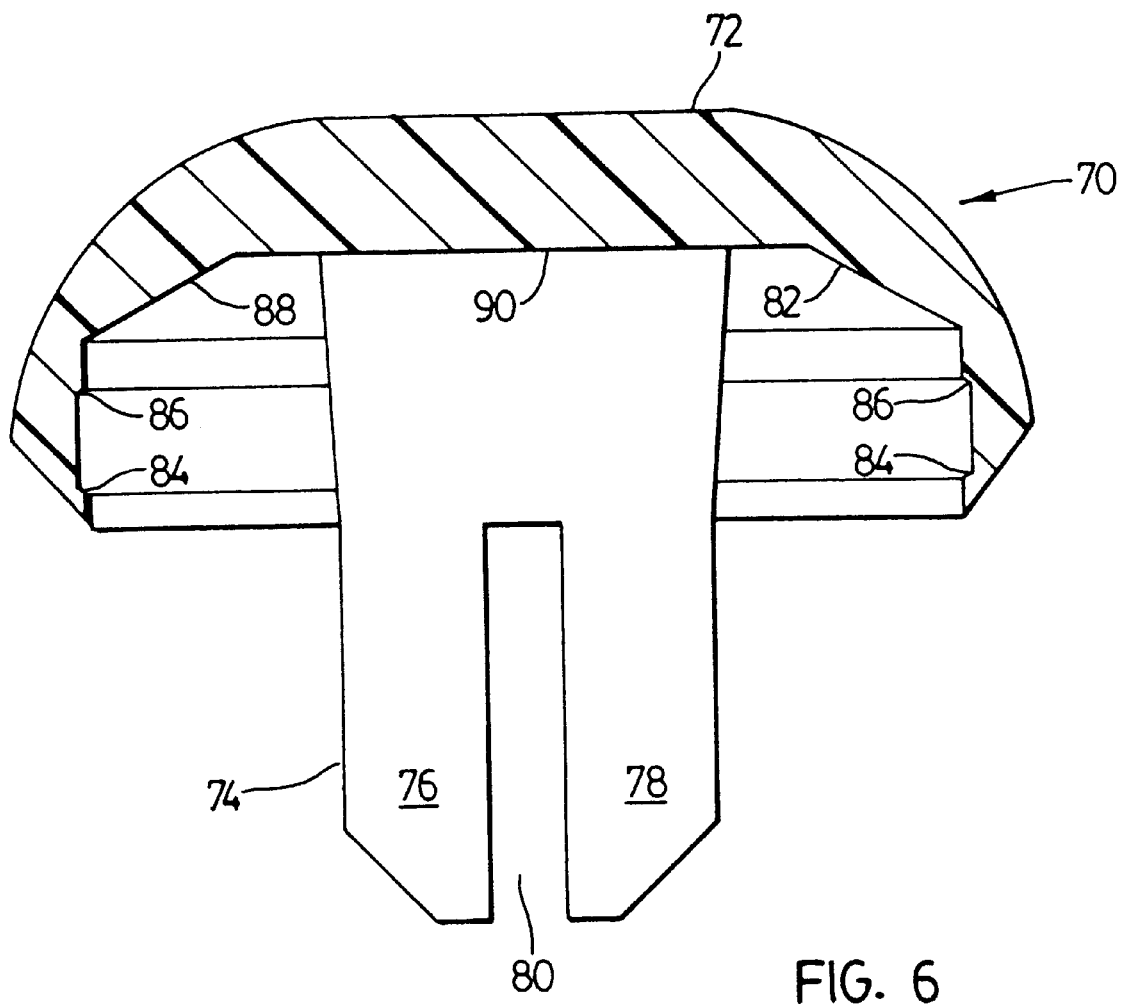
FIG. 6 is a side view of a healing cap for use in association with the implant of FIG. 1.

FIG. 6 shows a healing cap which may be used to protect the keyway 30 while the bone is healing and growing into the implant prior to an abutment portion 50 or 40 being inserted. The healing cap is identified generally at 70 and includes a coronal portion 72 which is gently curved and a keyway portion 74 which is intended to be press fit into the keyway 30. The keyway portion 74 is comprised of two limbs 76 and 78 separated by a groove 80. By means of the groove, the portion 76 and 78 may be compressed inwardly into the keyway 30 and securely retained in position.

It will be also noted that the healing cap 70 includes an insert portion 82 which accommodated the upper part of the coronal portion 12 of the one piece implant. The surfaces 84, 86, 88, and 90 are intended to cover and capture the coronal portion of the implant. By means of the inward angle of the portions 84, the healing caps snaps into place over top of the coronal portion of the one piece implant 10. In this ;manner, the healing cap is securely held in place in addition to the compression of the keyway portions 76 and 78. Preferably the healing cap 70 is made of a polymer material for flexible retention in the coronal portion.

Figure 7:
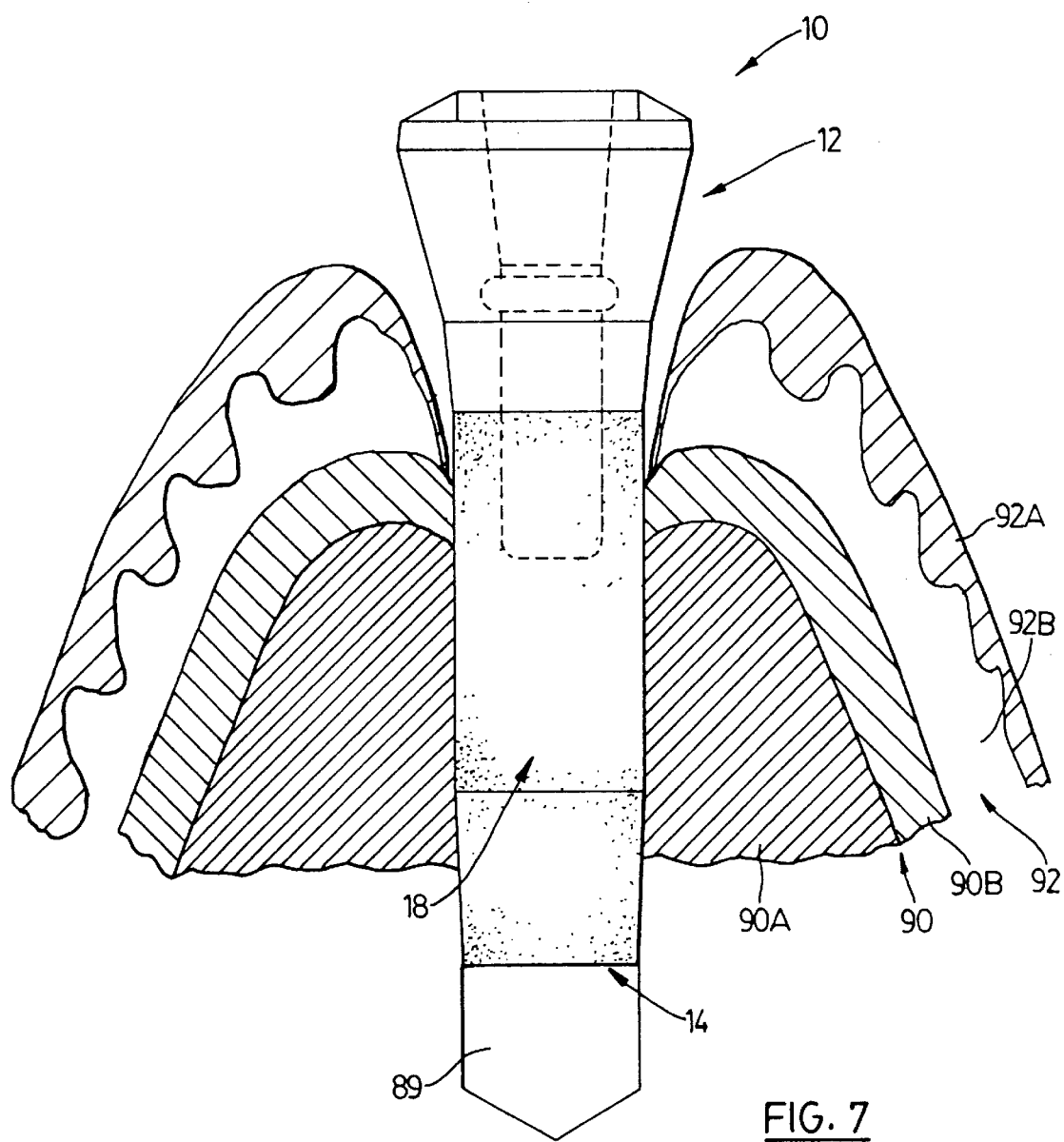
FIG. 7 is a view of the implant partially inserted.
Figure 8:
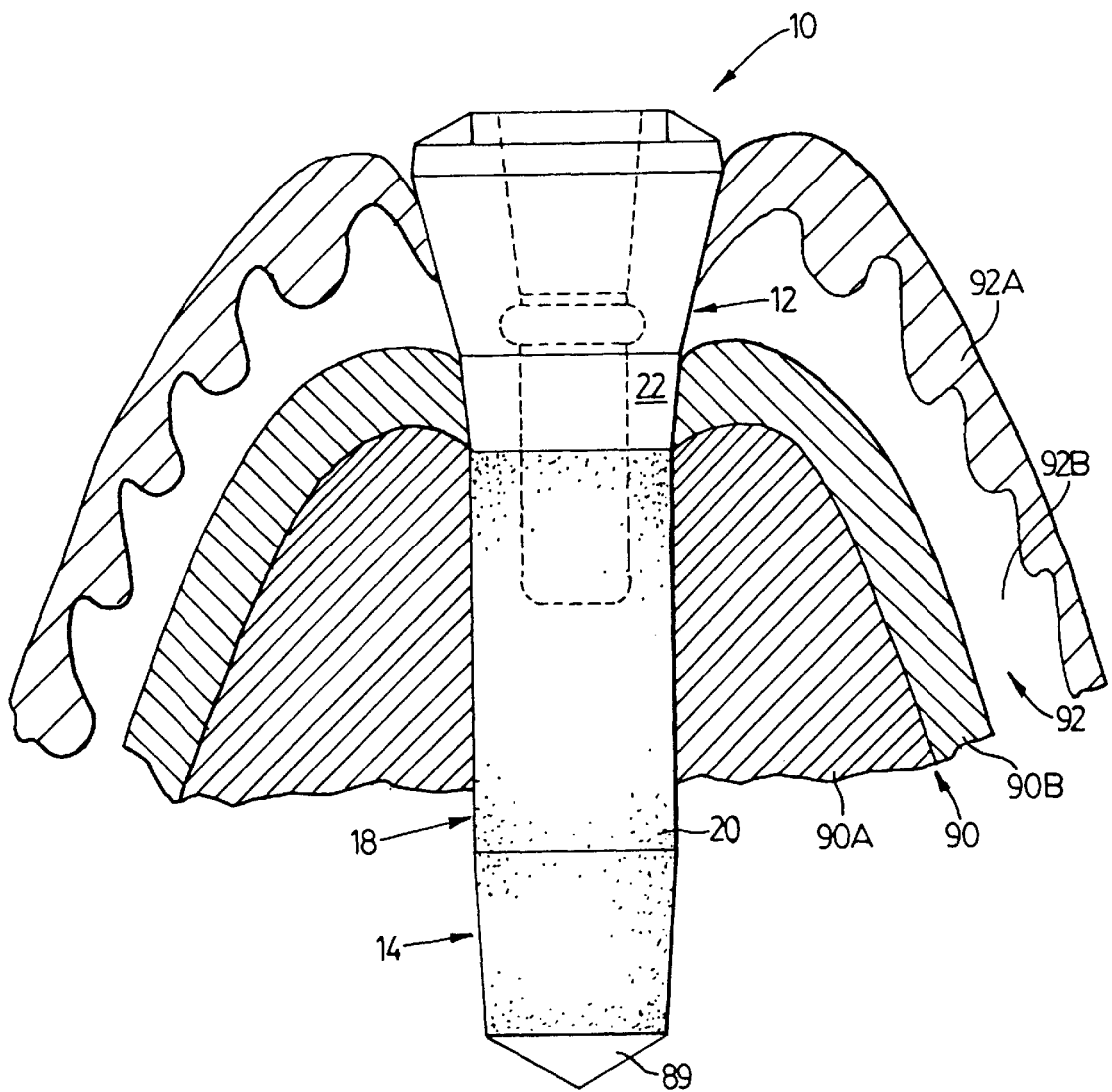
FIG. 8 is a view showing the implant of FIG. 1 in an installed position.
Figure 9:
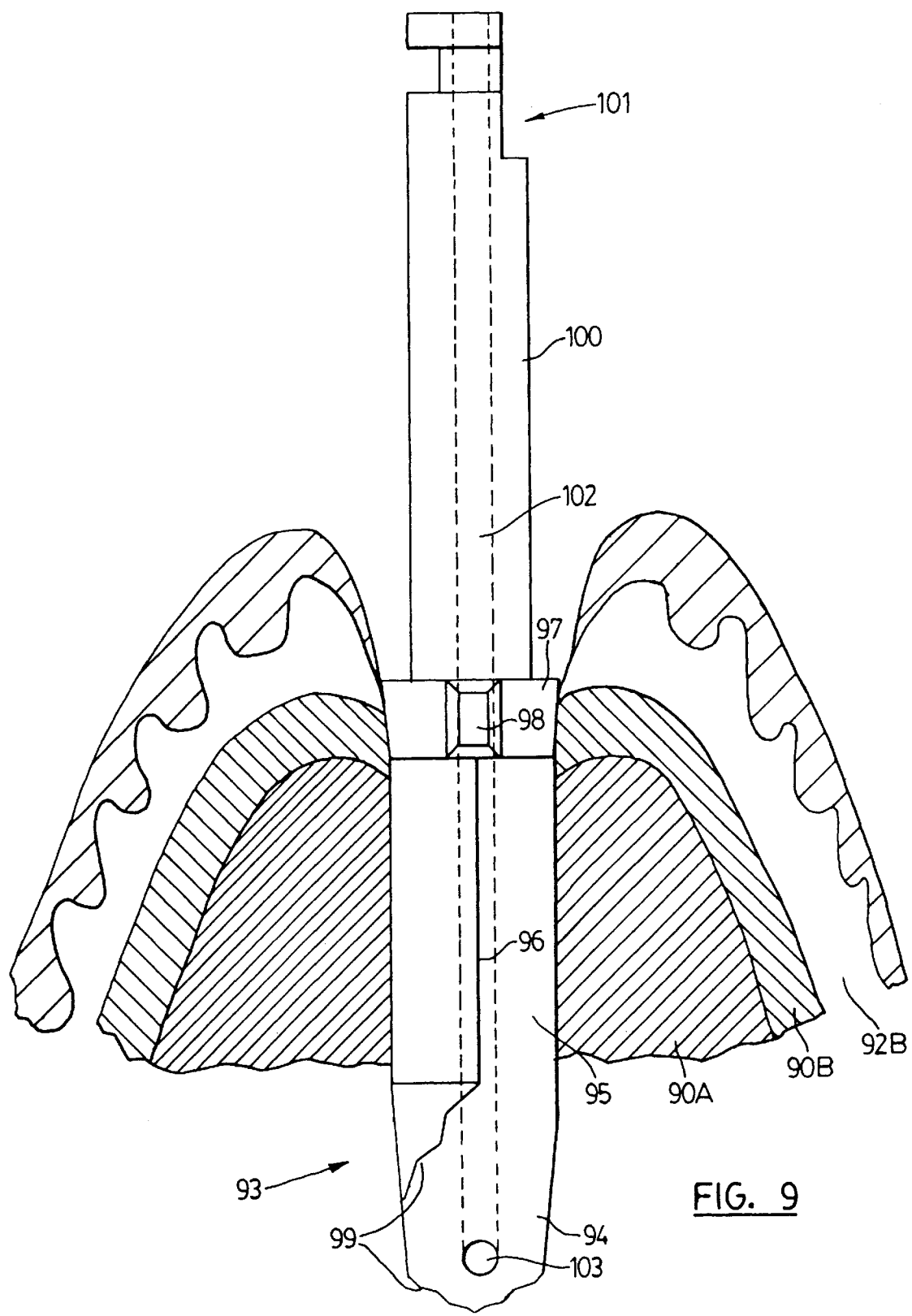
FIG. 9 is a view of a drill for inserting the implant of FIG. 1.

With references to FIGS. 7–9, it can now be appreciated how the implant of the present invention may be installed.

The first step is to identify the site into which installation is to occur. As will be understood by skilled practitioner, the necessary ground work to prepare for installation will involve the obtaining and careful analysis of X-rays or other suitable imaging techniques to enable a full understanding of the implant site to be gained. Once the location has been identified then it becomes necessary to identify the appropriate insert. It will now be appreciated that by forming the preferred implant with a cylindrical section 18 above the tapered apical portion 14 the implant length can be varied according to site conditions. While the preferred axial length of the tapered apical portion is 0.12 in. (3.00 m.m.), the cylindrical section 18 can be made 0.14, 0.26, 0.37 or 0.49 in. (3.50, 6.50, 9.50 or 12.5 m.m.). This can then provide to the practitioner a range of implant depths to choose from again according to site specifics. In general, providing there is adequate integral bone the larger depths are preferred.

Block et al. writing in J. Oral Maxillofac. Sur. 48: 174–178, 1990 and Stultz et al. writing in Compen. Contin. Educ. Dent., Vol XIV, No. 4, 478–486, and Walmsley have shown that implant success is directly proportional to implant length.

Once the proper length has been selected it is then necessary to prepare the gingival 92 and bone 90 for the implant 10 (see FIG. 7). This is accomplished by, after adequate anesthetic of the patient, drilling a single recess 89 into the installation site. It is noted that the bone 90 of the installation site is generally composed of a soft cancellous portion 90A and a hard cortical portion 90B, and the gingiva 92 is generally composed of a gum 92A and the sub-gum or derma 92B.

According to the present invention only a single final drill bit 93 need be used as shown in FIG. 9. The drill bit 93 has a tapered section 94 and a cylindrical section 95. It will be appreciated that the shape and dimension of section 94, 95 of the drill bit should closely correspond to that of the selected implant 10. However, it is preferable for the tapered section 94 to be just slightly longer than the corresponding implant, for example by 0.03 in (0.75 m.m.), for ease of fit.

The cylindrical section 94 has opposed cutting edges 96 (only one of which is shown). A tapered coronal portion 97 has one or more discrete, protruding cutting teeth 98 thereon. The taper on the coronal portion 97 may be referred to as the "third paper". Reference numeral 99 indicates another set of cutting edges on the tapered section 94 (which has three or four sets of such edges, as desired). A smaller diameter upper portion 100 of the drill 93 has a keyway adapter 101 at its top end for engaging a drive mechanism of a dentist's drill (not shown). A hollow stem or bore 102 extends through the drill 93 along its length, as shown. A saline coolant is delivered from the drill to an opening 103 though the bore 102 to cool and drill bit and prevent heat build up, which heat could damage the living cells being drilled into.

The use of the single final drill 93 is preceded by the use of a conventional smaller pilot drill (not shown). The pilot drill also has a hollow stem or bore to allow internal irrigation with normal saline solution. Additionally, external irrigation may be used (for both drills) to cool the site being drilled to prevent damage to the bone tissue during the site preparation.

The drill 93 of the present invention differs from prior art systems which use a parallel sided final drill, either with a hollow stem or with a solid stem (which permits external irrigation only). The tapered portion of the surgical site is prepared after, by a separate drill, thus allowing no control over the length of the midsection portion of the bone hole.

Once the recess 89 in the bone has been drilled, it will have a tapered apical portion. Referring back to FIG. 7, an implant 10 according to the present invention is shown being installed into the recess 89 in the bone 90 and the gingiva 92 after the bone has been drilled. As can be seen, the lower section of the recess 89 tapers slightly, preferably in an amount less than 5°, over the depth of 0.12 in. (3.00 m.m.).

FIG. 8 shows the implant in the fully installed position. To attain this position it is necessary to press the implant into the bone 90, by reason of the interference fit between the bone 90 and the implant 10. This is preferably accomplished by gently tapping the coronal portion 12 of the implant to firmly seat the implant into the bone. Thereafter the haling cap 70 is installed and the patient is allowed to leave. A suitable period of a few months is allowed to elapse and then the patient can return for installation of an appropriate abutment portion. Those skilled in the art will appreciated that the two styles of abutment portions provided according to the present invention are conventional above the gum line and thus will be readily understood and used by practitioners.

At this point an important aspect of the invention can be better appreciated, namely how the implant 10 of the present invention and the bone 90 interact. When the implant 10 is tapped into the recess 89 as shown in FIG. 8, the smooth-walled (i.e. emergent) portion 22 causes the implant to initially be wedged into the hard cortical portion 90B of the jaw bone 90 to stabilize the implant in the recess 89. This wedging arises because of the taper of emergent portion 22 and because the diameter of the emergent portion 22 is slightly larger than the diameter of the recess, and is not due to any surface effects between the cortical bone 90B and the smooth biocompatible surface on emergent portion 22. During the ensuing months, the soft cancellous portion 90A of the jaw bone gradually grows into the coating 20 and attaches to the cylindrical section 18 of the implant. In the meantime, the cortical portion 90B slowly subsides away from the smooth biocompatible surface of the emergent portion 22. Hence, the biocompatible surface of the emergent portion 22 only temporarily helps hold the implant 10 in place while the cancellous portion 90A bonds to the cylindrical section 18. It is believed that the stress induced into (i.e. the displacement of) the cortical portion 90B by the taper of the emergent portion 22 is insufficient to prevent the cortical portion 90B from subsiding and remoulding away from the implant.

Figure 10:
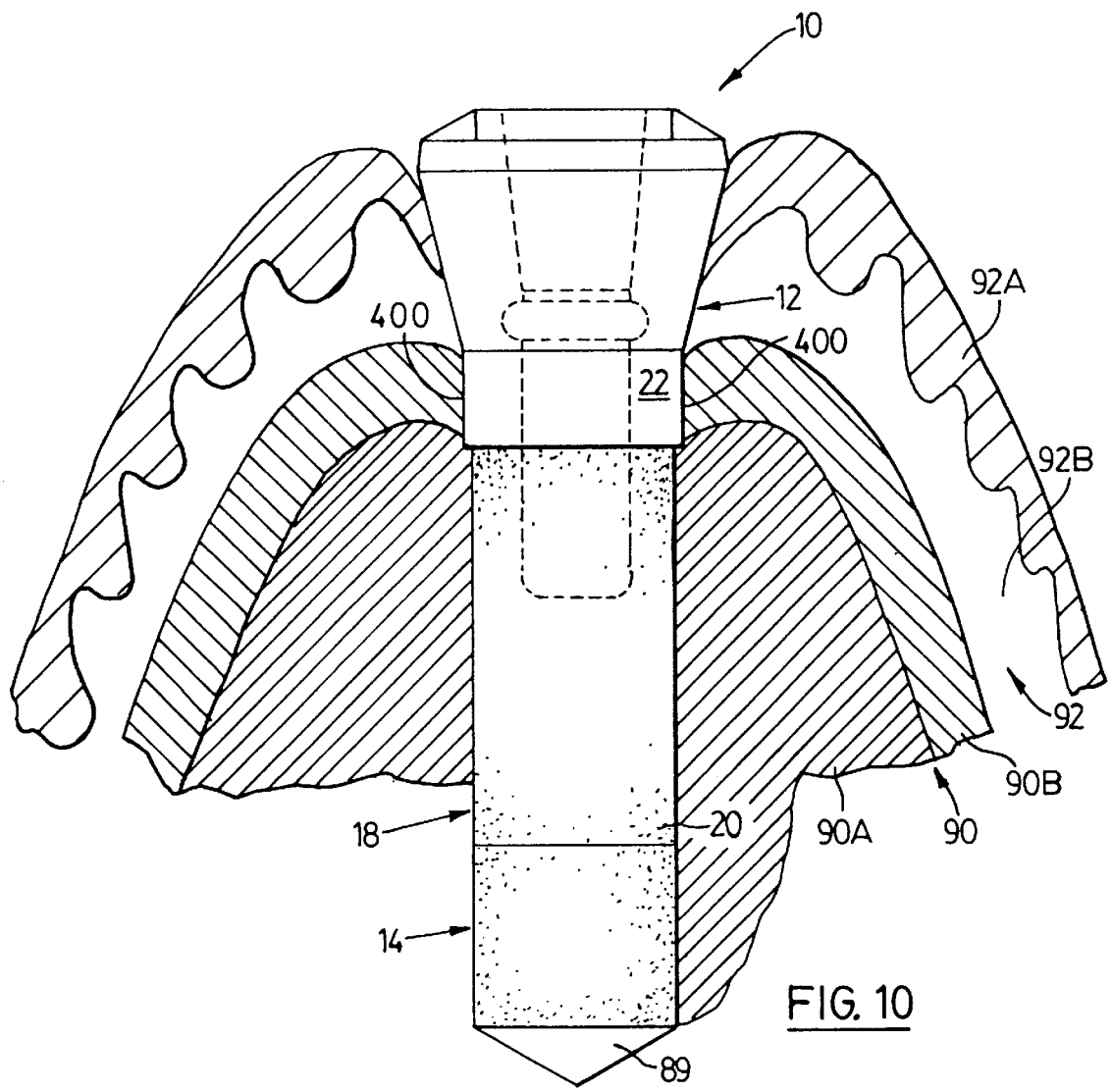
FIG. 10 is a view of an implant according to a second aspect of the present invention.
Figure 11:
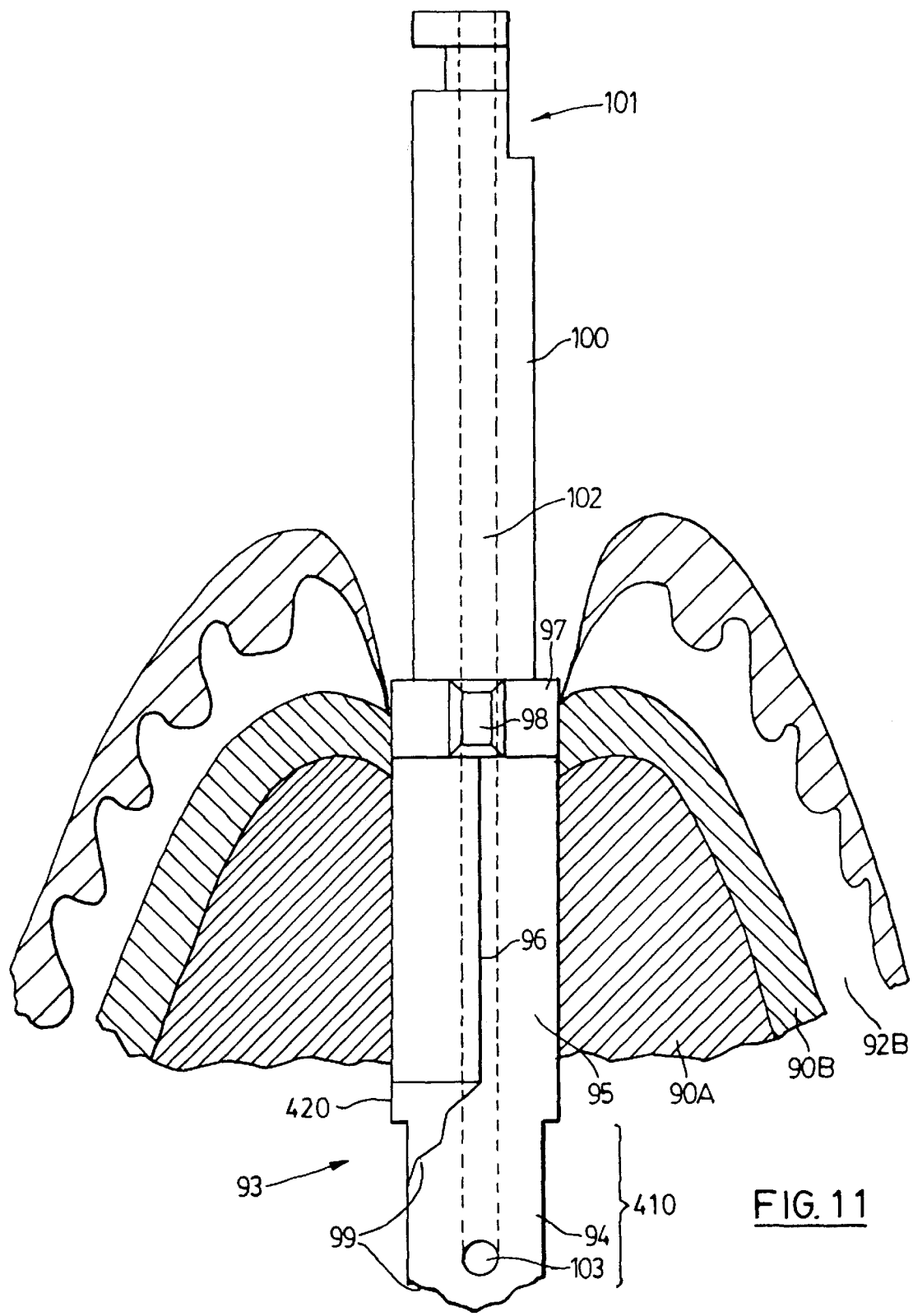
FIG. 11 is a front view of a drill for inserting the implant of FIG. 10.

FIGS. 10 and 11 show a further embodiment of the present invention, in which like reference numbers refer to the same components. While achieving an interference fit between the implant and the cortical bone section at the emergent portion 22 of the implant 10 and the implant and the cancellous bone section at the root portion 14 with a wedge or taper fit yields satisfactory results, there is also a drawback with such a taper. More specifically such a taper acts as a wedge which if forced too hard during implantation by an unskilled practitioner can lead to a splitting or fracturing of the bone. Thus the present invention also contemplates an interference fit between the emergent portion and the cortical bone by means of a straight walled step as shown at 400 in FIG. 10. The step is dimensioned to fit, in an interference manner in the hold drilled in the bone. The width of the step is dimensioned to exert a significant gripping force on the one hand, without exceeding the typical fracture stresses for such bone on the other. Different degrees of step or size of interference fit would be provided for different patients, with older patients having more brittle bones being treated with implants having a narrower step than for younger patients with stronger bones. In general to ensure a secure fit in the cancellous region, which is generally a softer bone, a slightly greater step or interference fit is necessary in this region. The step function at the emergent portion is preferred to be between 0.01 mm and 0.10 mm and at the cancellous bone region between 0.01 mm and 0.15 mm. Step function in this sense refers to the amount by which the implant is bigger in outside diameter than the inside diameter of the bore or hole into which it is being inserted. It will be appreciated that forming an interference fit can be done by making the implant bigger than the bore into which it is inserted, by making the implant bigger than the drill diameter, or the drill smaller than the implant diameter. To form an interference fit in the apical portion or root portion 14 will require forming an initial bore of a slightly smaller diameter than the following bore, which can easily be accomplished by a drill having a smaller diameter tip 410 than a trailing section 420 as shown in FIG. 11. The width of the shoulder on the drill will be such as to form a good interference fit in the cancellous bone section. In some case it may be preferred to provide a taper at the apical end of the implant together with a step at the emergent portion, to minimize the risk of forming pockets or gaps around the apical portion 14 of the implant.

It will be appreciated that the step design will prevent the implant from being installed in a manner which is likely to cause a bone fracture. Further, the depth of the implant can be more easily varied in the hole than with a tapered design. All that is required to press the implant into the bore more is to overcome friction; with a taper, deeper penetration could lead to fracturing the bone. Thus the stepped design is preferred in some applications.

It will be understood that his second embodiment works according to the same principles as the previous embodiment in that the implant upon being implanted will press fit into the bone at the emergent portion 22 and at the root portion 14 to retain the implant in a secure position to allow bone ingrowth to occur over the straight walled root portion 18. The straight walled root portion will not necessarily be an interference fit, but merely closely fit to allow bony ingrowth to occur. Thereafter the bone adjacent to the press fit sections will likely subside, in part as a reaction to the unnatural stresses being imposed upon it by the press fitting action of the implant. As the cortical bone subsides next to the press fit section of the emergent portion 22, it is simultaneously growing into the straight walled root portion, thereby forming a secure and stable attachment to the patient.

Figure 12:
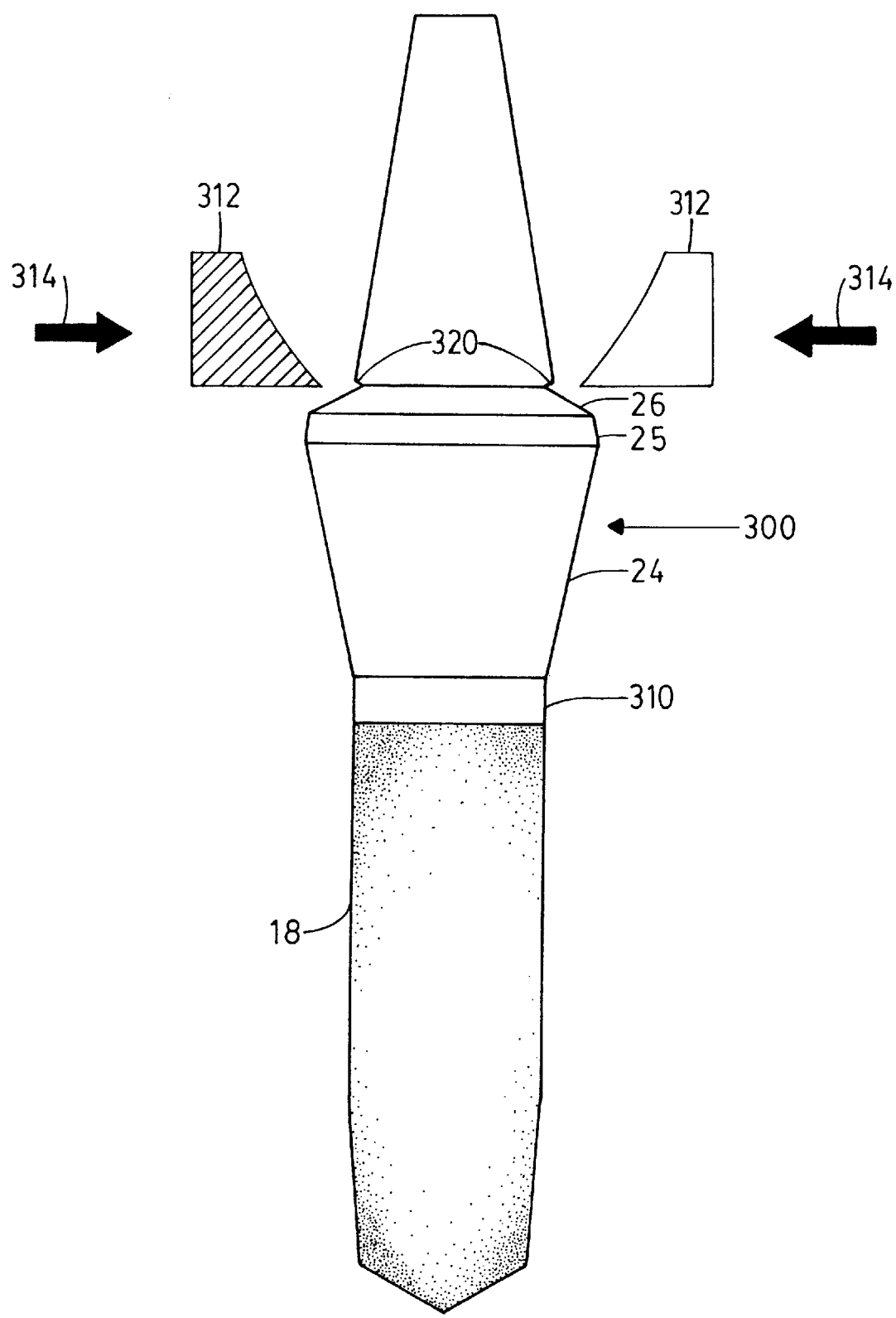
FIG. 12 is a side view of a third embodiment of an implant according to the present invention.
Figure 13:
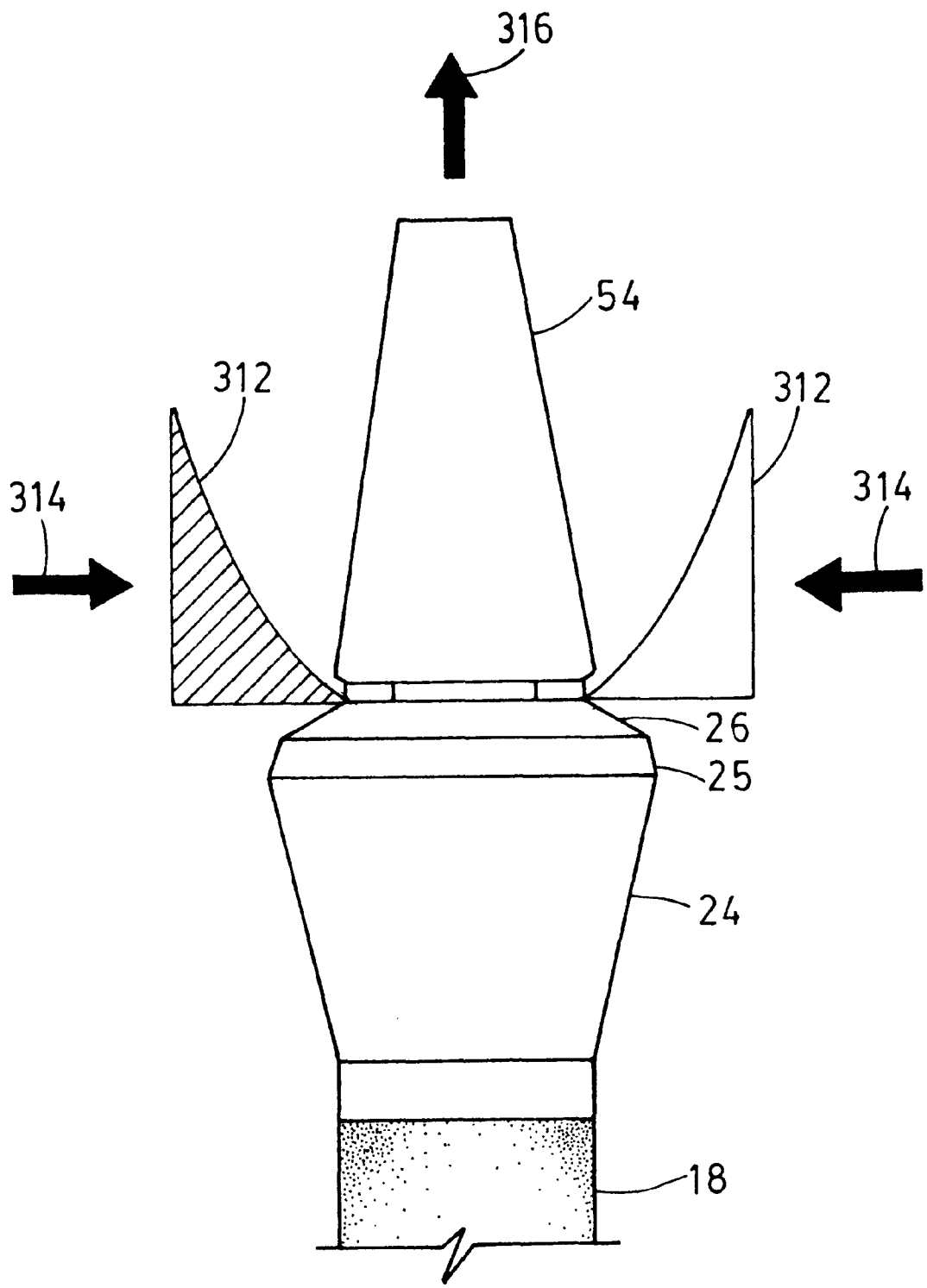
FIG. 13 is a side view of the second embodiment showing how the abutment portion may be freed.
Figure 14:
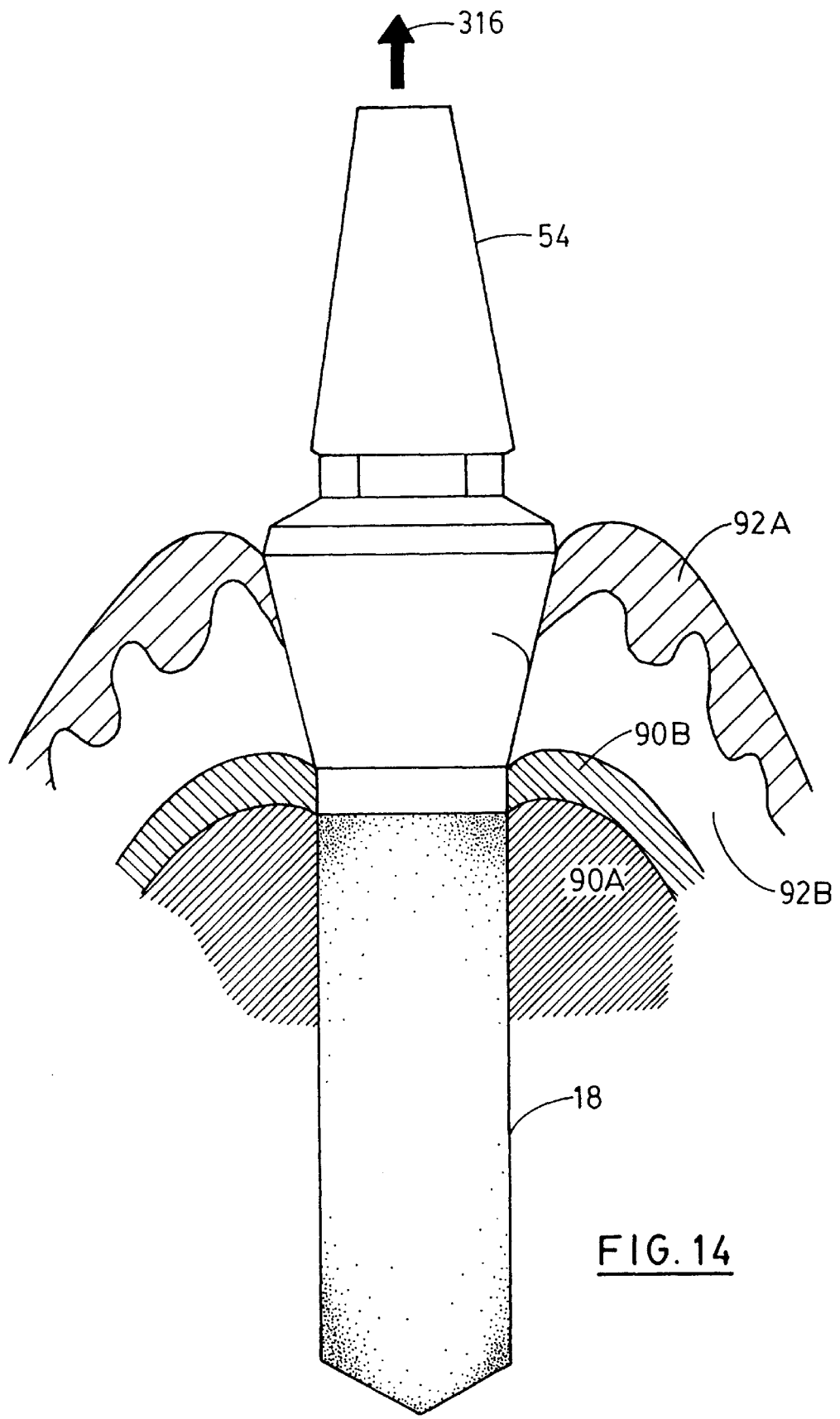
FIG. 14 is a side view of the second embodiment of FIG. 13 showing the abutment portion coming free.

FIG. 12 is a side view of a third embodiment of the present invention, shown generally as 300. In FIG. 12, 13 and 14, like numerals refer to like components as in the previous embodiment. In this embodiment, the cylindrical section 18 is similar to that of the previous embodiments, but rather than tapering at 22 as in the first embodiment, or including a step as in the second embodiment, in the third embodiment, the smooth-walled portion, shown as 310, is also cylindrical and of the same dimension as the root portion. This, is certain implant circumstances, has some clear advantages. The primary advantage is that by replacing the welding taper, the potential for splitting the bone coronally is reduced. Of course, the smooth-walled portion 310 is sized and shaped to correspond to the outside diameter of the cylindrical root portion 18. In the case of a cylindrical root portion 18, the bore formed in the bone will be such that a smooth friction fit between the root and the bone is established. In this sense, the friction fit needs to be sufficient to secure the implant in place for initial stabilization.

Longer term stabilization, occurring through bone ingrowth, achieves a three dimensional locking between bone and implant by reason of the porous coating.

Another feature of the third embodiment is the extension of the cylindrical root portion fully down the length of the implant, whereby the lower tapered section 16 of the previous embodiments is removed. Adequate results have been achieved with a cylinder of between 3.55 and 3.75 mm in diameter, with a preferred diameter of 3.64 mm. The advantage of such a cylindrical geometry is that is increases the surface area in this region (what was section 16), over the surface area of the taper, by about 9.6%. By increasing the surface area, a better and stronger bond is possible between the bone and the porous coating. Quite simply, the larger the surface area, the more bonding can take place. For a drilled bore, the maximum surface area is a true cylinder which is what this third embodiment uses.

Another feature of the third embodiments is to slightly increase the overall diameter of the implant, which also increases the overall intraossesous surface area. For example, by increasing the cross sectional diameter to 3.64 mm increases the intra osseous surface area by about 5.5% which again gives a better implant by bore bond. In this regard, one of the key advantages of the third embodiment remains its generally narrow diameter. It is believed that bone resorption, post implantation, is influenced by how much bone mass is left around the implant. Thus, implants with large coronal diameters, at the location where the implant emerges from the bore, may tend to suffer more bone loss, because the larger diameter hole required. Thus, slightly increasing the diameter of the implant root portion is desirable to increase surface area, but this must be balanced against the need for as small a root portion as practical, given strength and other considerations. Thus, the preferred diameter is about 3.64 mm for the cylindrical root portion (including the porous coating).

A further feature of the third embodiment is the formation of a slight overhang 320, at the interface between the abutment portion and the root portion. In this manner a pair of orthodontic wire cutters can be used shown as 312 in FIG. 12, by applying force (arrows 314) below the over hand 320 as shown in FIG. 13, to pry out the abutment from the root portion (arrow 316). In this sense the small gap between the abutment portion and the root portion is like a notch, into which the sharp edge of the wire cutters may be applied, as shown. In this manner, the abutment is made more easily retrievable, and, as soon as the cement bond is broken, the abutment comes easily free as shown in FIG. 14.

To facilitate this feature it is preferred to radius the lower corners of the abutment portion, as shown, to permit the wire cutters to be inserted into the interface and to exert and upward thrust component, isolated on the abutment portion, as shown. In this manner the abutment portions are made retrievable, to facilitate repositioning the prosthetic to accommodate bit changes and the like occurring in the patient. Further, the abutments may be retrieved without disturbing the bone implant interface.

It can now be appreciated that the method of installing the third embodiment, while generally similar, is also different from the first two embodiments. Primarily, the third embodiment is a time saving simpler procedure. Because the recess formed around the pilot hole is cylindrical, no extra drills or drilling steps are required. To implant, one simply forms the pilot hole, drills a cylindrical recess with a second drill, to a predetermined depth corresponding to the depth of the cylindrical root portion, and then inserts the implant into the recess. Of course, the cylindrical recess is sized and shaped to form a frictional fit to permit initial implant stabilization of the implant during bone ingrowth. A healing cap may also be used as previously described.

It will be understood that the third embodiment described above works in accordance with the same general principles as the previous embodiments, with the exception that no step or taper is required to press fit the implant into the cylindrical recess in the bone. The method is simpler and less time consuming, but otherwise the principles are the same. By reason of a frictional fit, initial implant stabilization is achieved, in a one stage implant surgery. A narrow diameter bore is used, to minimize bone disruption during surgery and to promote good bone growth post surgery. A cylindrical profile for the full root portion 18 and the smooth-walled emergent portion 22 maximize surface area for bonding. Bone resorption is reduced because of the larger bone mass remaining post surgery, as compared to other implant profiles which show larger diameter bone emergent portions.

It will be appreciated by those skilled in the art that the foregoing description is in respect of preferred embodiments and that various modifications can be made to in the invention without departing from the broad scope of the appended claims. Some of these modifications have been suggested above, and others will be apparent to those skilled in the art. For example, the head portion 44, 54 may be angled relative to the key portion 42, 52, respectively, to allow the location of the implant to be varied based on site conditions without displacing the over denture or bridge. The angle by which the head portion and the key portion may be angled is between 15° –35°. Also, the precise dimensions may be modified without changing the operation of the invention. And finally, while the invention has been described in association with over dentures and bridges, it will be appreciated that it can be used to secure other cosmetic devices, such as artificial ears or eyes where an anchor is necessary in bone.

The embodiments of the invention in which an exclusive property or privilege is claimed are defined as follows:

1. An implant for anchoring a prosthetic device in bone said implant comprising:
   a) a one piece body having a cylindrical intra osseous portion and a transgingival portion, said cylindrical intra osseous portion including a porous coated root portion and a smooth-walled emergent portion, said transgingival portion including a keyway; and
   b) a cementable abutment portion for insertion into said keyway, said cementable abutment portion including a key at one end for insertion into said keyway, said key and said keyway being sized and shaped to provide cement space therebetween, said cementable abutment portion also including a head at the other end for retention of said prosthetic device, and a shoulder, on said head, said shoulder being sized and shaped to permit said cementable abutment portion to be pried off said body when cemented thereto.

2. An implant as claimed in claim 1 wherein said abutment portion meets said coronal portion at an interface, and in the installed position, the interface is beyond a gingival layer to allow access to said interface.

3. The dental implant of claim 2 wherein said keyway is asymmetrical in cross section to prevent rotation of said abutment portion relative to said one piece body.

4. The dental implant of claim 1 wherein said root portion may be made from one of a number of lengths to accommodate different implant location conditions.

5. A method of inserting a dental implant comprising:

incising through a gingival layer;

drilling a pilot hole with a first drill bit at an appropriate location into a bone located below said gingival layer, drilling a cylindrical recess, about said pilot hole, into the bone with a second drill bit, gently tapping said implant in frictional engagement with said bone wherein said step of tapping includes seating said implant against a bottom of said recess;

allowing said bone to grow into a root portion of said implant, and cementing a retrievable abutment to said implant.

6. The method of inserting a dental implant as claimed in claim 5 wherein said implant includes a cylindrical root having a predetermined length, and step of drilling a cylindrical recess to a depth which corresponds to the predetermined length of said implant.

7. The method of claim 6 wherein said step of allowing the bone to grow includes providing a healing cap between the time the insertion is made and the abutment portion is secured.

8. The method of claim 5 wherein said cylindrical recess is sized and shaped to frictionally engage a cylindrical root portion of said implant, to permit initial implant stabilization during bone ingrowth.

\* \* \* \* \*